United States Patent [19]
Hayes et al.

[11] Patent Number: 5,364,397
[45] Date of Patent: Nov. 15, 1994

[54] SPINAL COUPLER SEATER WITH DUAL JAWS AND AN INDEPENDENT PLUNGER

[75] Inventors: S. Kyle Hayes, Laguna Niguel, Calif.; Randall N. Allard, Plymouth, Ind.

[73] Assignee: Zimmer, Inc., Warsaw, Ind.

[21] Appl. No.: 69,497

[22] Filed: Jun. 1, 1993

[51] Int. Cl.$^5$ ............................................. A61B 19/00
[52] U.S. Cl. ............................................. 606/61; 606/1; 81/300
[58] Field of Search ............... 606/1, 60, 61, 205–209, 606/210, 211; 29/268, 243.56, 229, 244, 248, 259, 261–268; 81/300

[56] References Cited

U.S. PATENT DOCUMENTS

| | | | |
|---|---|---|---|
| 3,175,556 | 3/1965 | Wood et al. | 606/142 |
| 4,347,845 | 9/1982 | Mayfield | 606/61 |
| 4,409,968 | 10/1983 | Drummond | 606/61 |
| 4,572,179 | 2/1986 | Teitelbaum et al. | 606/207 |
| 5,022,292 | 6/1991 | Hammer et al. | 29/268 |
| 5,242,445 | 9/1993 | Ashman | 606/61 |

FOREIGN PATENT DOCUMENTS 0608564 11/1960 Canada ................... 29/268

*Primary Examiner*—Stephen C. Pellegrino
*Assistant Examiner*—Glenn K. Dawson
*Attorney, Agent, or Firm*—Todd A. Dawson

[57] ABSTRACT

An instrument and method for locating and attaching a spinal coupler to an implanted spinal rod including body and lever handles that attach about the spinal rod. A cam handle is connected to the body handle to actuate a plunger that applies a compression force to the spinal coupler to attach it to the spinal rod by an interference fit. The body and lever handles each include a forked jaw having legs that attach to the spinal rod on each side of the spinal coupler. In one embodiment, the plunger includes a control knob to vary the instrument actuating force and prevent over extension of the plunger.

8 Claims, 4 Drawing Sheets

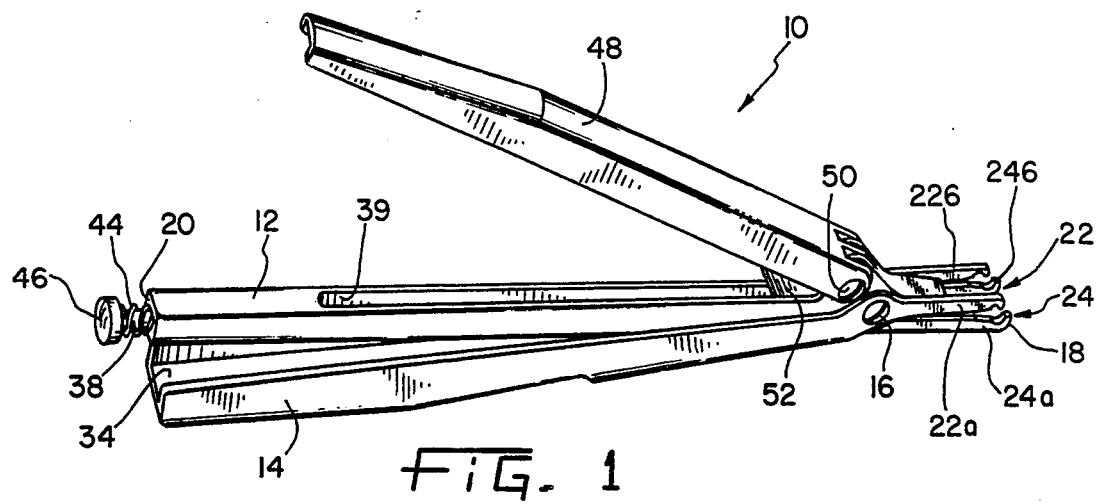
FIG. 1
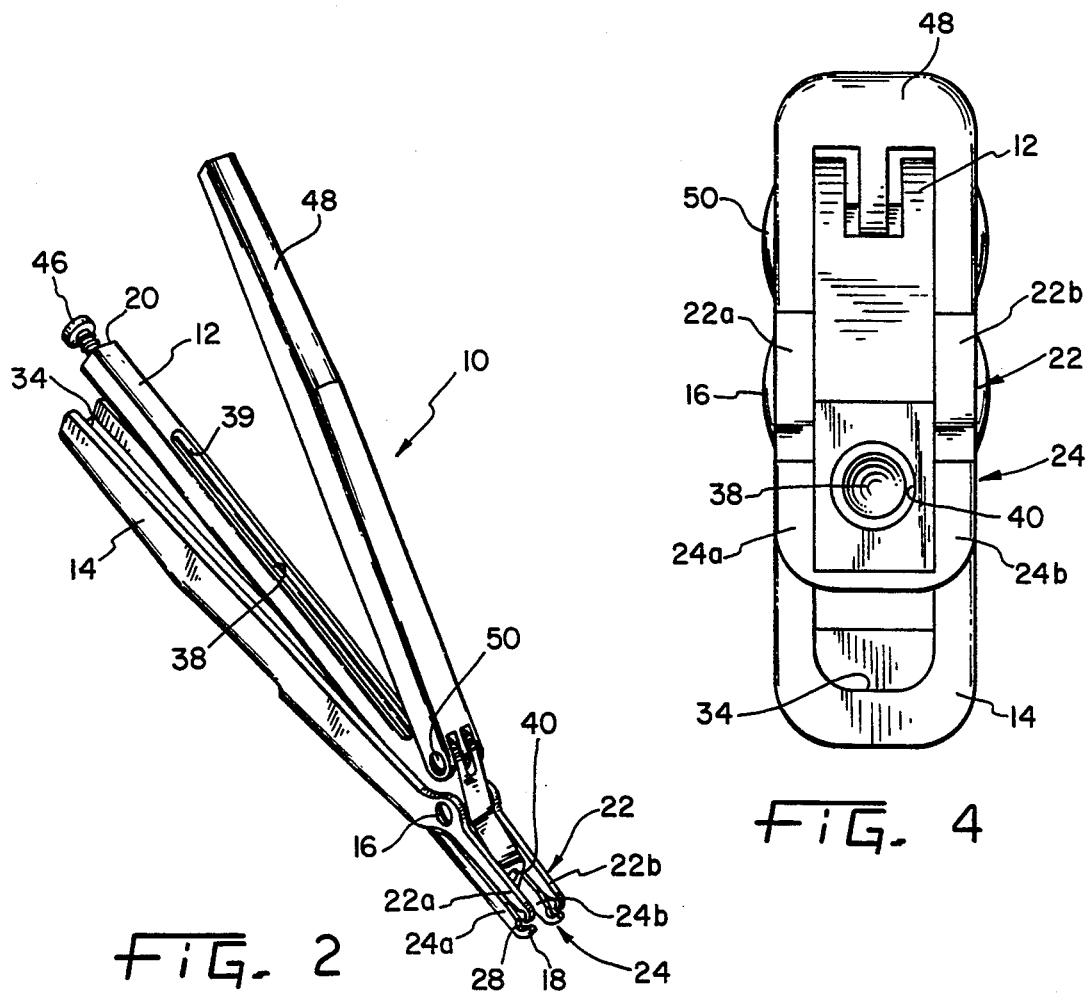
FIG. 2
FIG. 4

SPINAL COUPLER SEATER WITH DUAL JAWS AND AN INDEPENDENT PLUNGER

BACKGROUND OF THE INVENTION

The present invention relates generally to couplers for spinal rods and, more particularly, to instruments that clamp the coupler to the spinal rod.

A typical problem with attaching spinal rod connectors to implanted spinal rods is that there is limited space in which to work. This lack of space, in addition to the requirement for accurate location and attachment of the spinal rods and couplers, increases the difficulty and complexity of back operations.

A major problem in attaching couplers to spinal rods is that of applying sufficient force to attach the coupler without damaging the surrounding tissue. The need to prevent tissue damage is critical when operating near the spinal cord. At times, a large amount of pressure is needed, with pinpoint accuracy, to attach the couplers to the spinal rods.

Moreover, the connections between the implanted spinal rods and couplers are required to be extremely tight, without play. The connection between the parts has to be extremely rigid and tight because it would be deleterious to the patient for the couplers and rods to separate while implanted.

The present invention is directed to overcoming the aforementioned problems associated with spinal rods and couplers wherein it is desired to provide an instrument for engaging and locating the rod and coupler, and then attaching the rod coupler to the implanted spinal rod by a compression or clamping force.

SUMMARY OF THE INVENTION

The present invention overcomes the problems associated with spinal rod couplers by providing an instrument capable of locating the spinal rod coupler and rod together, and then attaching the coupler to the rod by an interference fit.

Generally the invention provides an instrument that includes a main handle connected in a scissor-like fashion to a lever handle. Opposed forked jaws or gripper portions connected to each handle come together to grip about an implanted spinal rod. A space between the forks of the jaws, receives the coupler and permits positive location of the coupler onto the rod. A cam handle, attached to main handle, pivots in a fashion to slide a plunger into contact with the coupler and compress the coupler about the spinal rod. The plunger slides within the main handle in a direction normal to the central axis of the spinal rod.

In one form of the invention, each jaw includes a ramped and grooved section on the inside edges opposing the other jaw to permit the spinal rod to slide into the groove when gripped by the instrument. The ramps permit the spinal rod to be automatically urged into the proper position. Accordingly, the instrument may be applied to the spinal rod in a casual fashion and automatically be urged into the proper orientation relative the implanted spinal rod.

In another form of the invention, a control knob is attached to the plunger to act as a stop to prevent overextension. The control knob also provides a visual indication that attachment is complete and that the spinal coupler is fully seated on the spinal rod.

An advantage of the spinal coupler seater of the present invention, according to one form thereof, is that of allowing the surgeon to operate the instrument in a one handed fashion while maintaining a positive gripping force on the rod.

Another advantage of the instrument of the present invention is that it permits the user to take two distinct motions of gripping the spinal rod and attaching the spinal coupler and combine them into one smooth motion. The first motion of gripping the spinal rod is accomplished by squeezing the instrument, much like using a pair of pliers. Additional squeezing on the instrument causes the plunger to extend and slide toward the spinal coupler and thereby compress and attach the spinal coupler onto the spinal rod.

Yet another advantage of the instrument of the present invention, in accordance with one form thereof, is that of a forked jaw design which engages the spinal rod and also locates the spinal coupler in place along the axis of the rod during the compression step. This forked design maintains the force from the plunger in a direction normal to the rod and coupler. A large amount of force may be accurately exerted on the spinal coupler and spinal rod without damaging nearby tissue.

Another advantage of the instrument of the present invention are two ramps along the inside of the gripping forks or jaws that cause the spinal rod to slide into the locating groove. The ramps permit the user to apply the instrument in a casual fashion and thereby automatically seat the instrument in a proper position on the spinal rod.

A further advantage of the instrument of the present invention is the provision for true compression force about the spinal rod, thereby eliminating the need to impact the coupler or rod assembly while it is disposed within the patient in order to attach the coupler.

A still further advantage of the present invention is of creating a simple and effective means of delivering the necessary force to attach a spinal coupler to a precise location on an implanted spinal rod.

The invention, in one form thereof, provides a surgical device for engaging a spinal rod and for coupling a spinal rod coupler to the rod. The device comprises an attaching means for securing the device on the spinal rod and locating the rod coupler on the rod and compression means for coupling the rod coupler to the spinal rod. The compression means operates by compressing the coupler onto the rod so that an interference fit is formed therebetween. The attaching means includes at least two jaws that grip the spinal rod and locate the spinal coupler between the jaws and the spinal rod.

In one form of the invention, the device includes a base handle and a lever handle connected in scissors-like fashion, so that an opposing jaw on each handle attaches to opposite sides of a spinal rod. An axial bore is formed in the base handle through which a plunger is slidable. A cam handle is hingedly attached to the base handle engaging the slidable plunger so that when actuated the cam handle causes the plunger to slide and press against the rod coupler thereby compressing the rod coupler onto the spinal rod creating an interference fit.

BRIEF DESCRIPTION OF THE DRAWINGS

FIG. 1 is a perspective view of the spinal coupler seater instrument of the present invention;

FIG. 2 is another perspective view of the spinal coupler seater instrument of the present invention;

FIG. 4 is an enlarged end view of the distal end of the instrument;

DETAILED DESCRIPTION OF THE INVENTION

Figure 3:
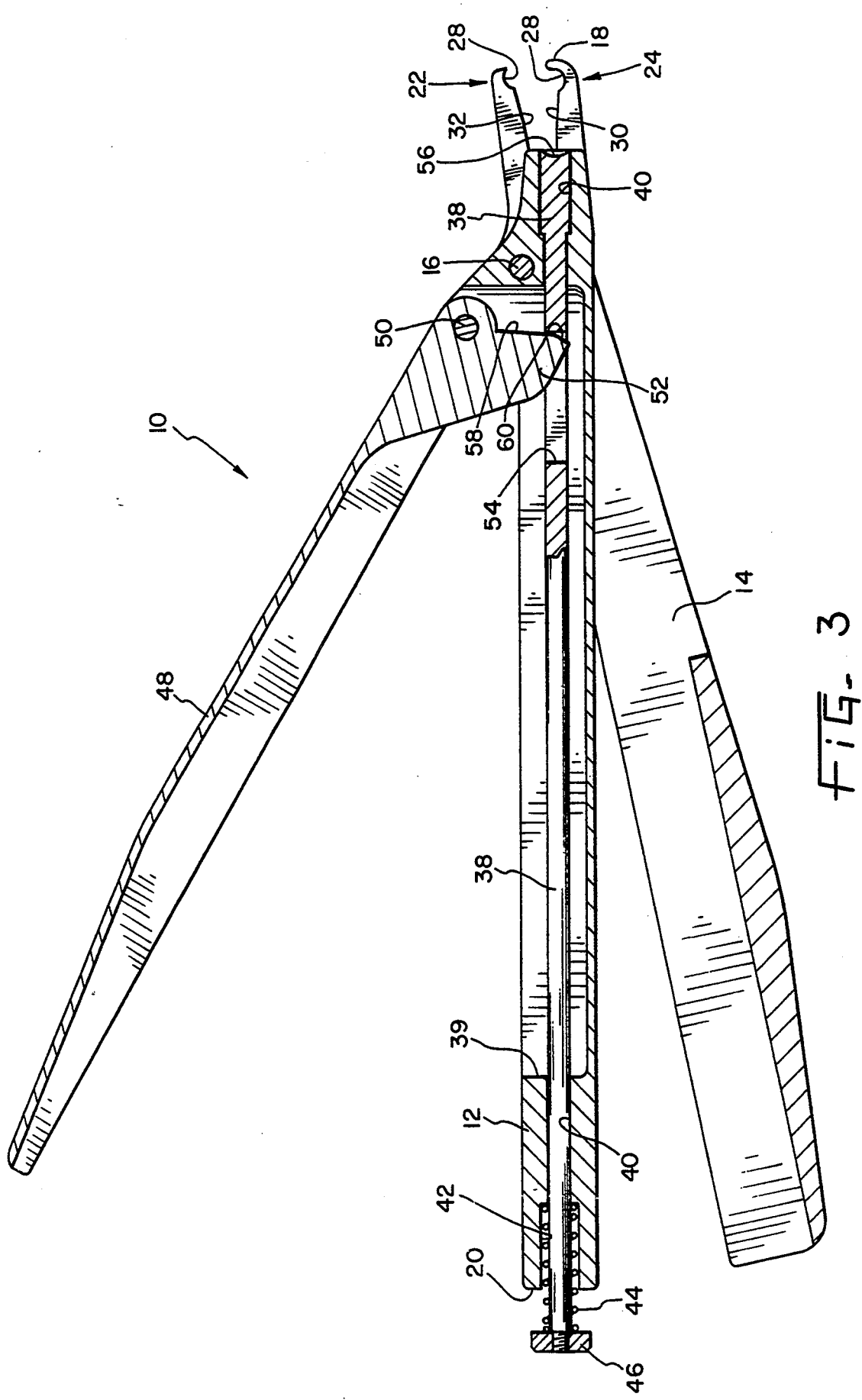
FIG. 3 is a longitudinal sectional view of the instrument.

Referring now to FIGS. 1–3, there is shown the spinal coupler seater instrument 10 of the present invention. The instrument 10 includes a main handle 12 pivotally connected to a lever handle 14 in a scissors like fashion about a pivot such as pin 16. Handle 12 includes a distal end 18 and proximal end 20. As shown in FIGS. 1 and 2, lever handle 14 includes a C-shaped channel 34 into which handle 12 may interfit when instrument 10 is compressed.

Figure 5:
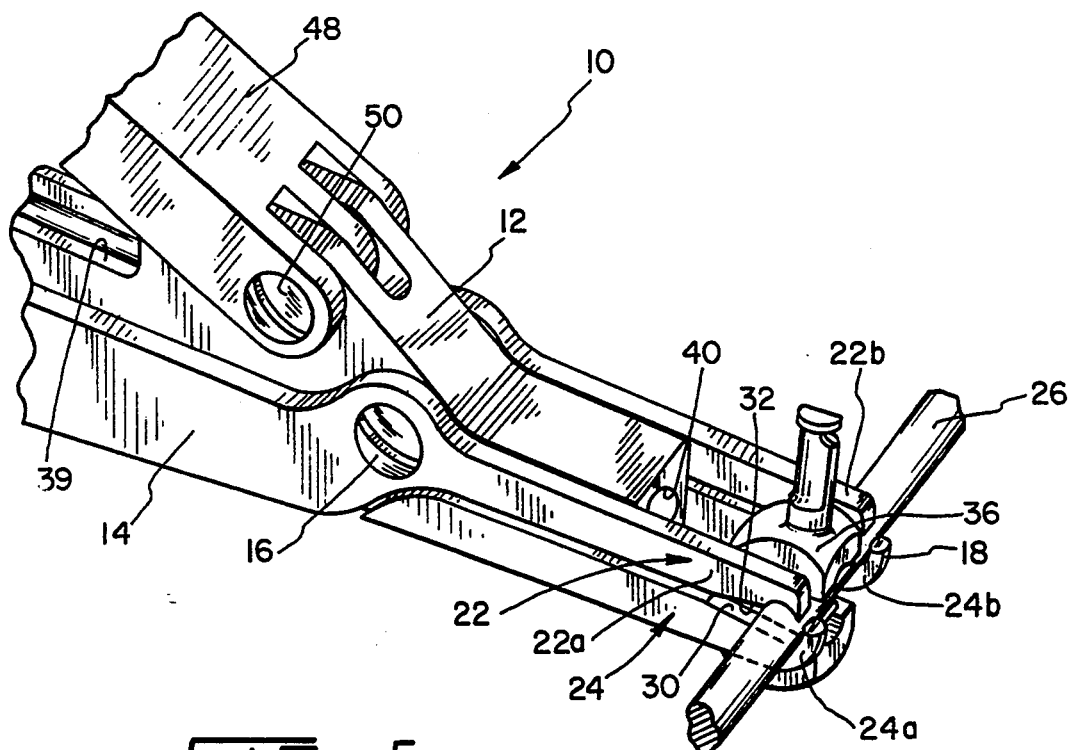
FIG. 5 is an enlarged perspective view of the instrument of the present invention secured to a spinal rod with a spinal coupler loosely disposed on the rod.
Figure 6:
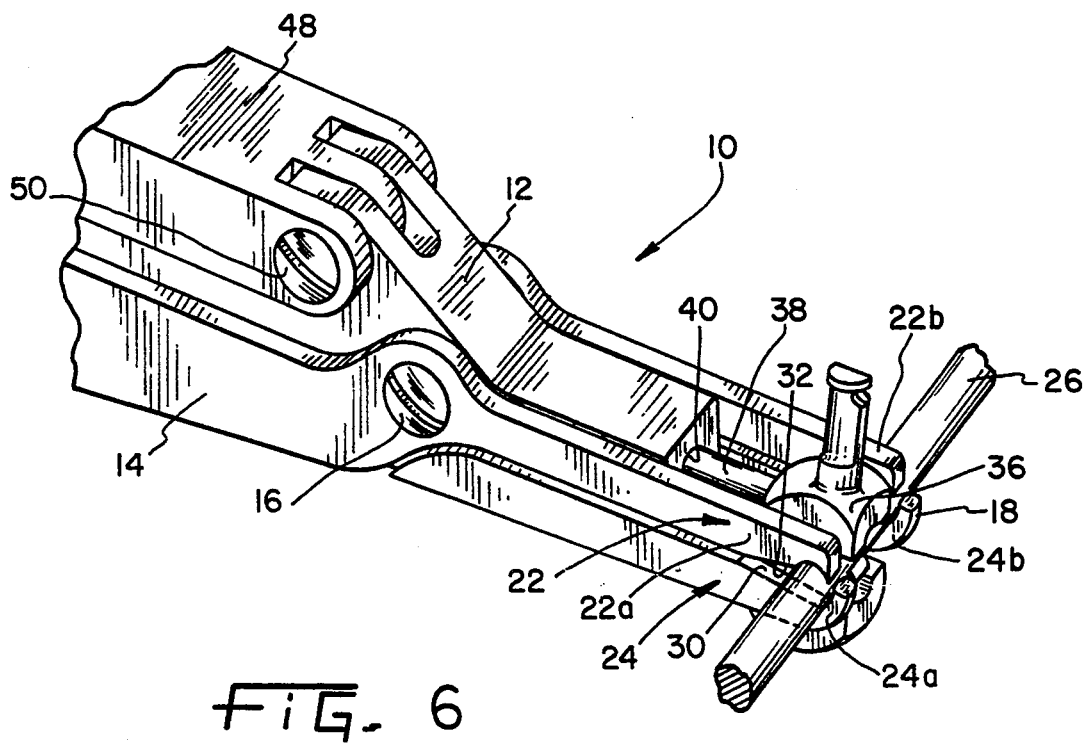
FIG. 6 is an enlarged perspective view of the instrument of the present invention shown with the plunger extended.

The handles 12 and 14 include an attachment means, such as forked jaws 22 and 24, for attachment of instrument 10 to spinal rod 26, as shown in FIGS. 5 and 6. Jaws 22 and 24 are part of lever handle 14 and main handle 12, respectively, and are opposed to grab opposite sides of rod 26. Each jaw 22 and 24 is forked, jaw 22 having legs 22a and 22b with jaw 24 having legs 24a and 24b. Each leg of jaws 22 and 24 includes a grooved portion 28 as shown in FIG. 3. These grooved portions 28 on each leg are sized to correspond with the diameter of a particular spinal rod 26 (FIG. 5).

Each jaw 22 and 24 further includes a ramp section 30 and 32, respectively. The angle of ramps 30 and 32 relative grooves 28 cause the rod 26 to slide into groove 28 when instrument 10 is clamped about a rod 26. The ramps 30 and 32 permit casual attachment of instrument 10 to rod 26 while forcing instrument 10 and rod 26 into proper orientation relative to each other. Moreover, instrument 10 is automatically oriented so that it is substantially normal to the axis of spinal rod 26 when clamped about rod 26.

Instrument 10 is designed to attach a spinal coupler 36 over a spinal rod 26 with an interference fit. Spinal coupler 36 is preferably one of a Modulock TM type design, manufactured by Zimmer, Inc., Warsaw, Ind. A full description of the preferred spinal rod coupler 36 is found in U.S. patent application Ser. No. 07/909,509, now U.S. Pat. No. 5,312,405, assigned to the assignee of the present invention and expressly incorporated herein by reference. Alternatively, other compatible spinal rod couplers maybe utilized with the present invention.

Spinal coupler 36 comprises a U-shaped yoke (FIG. 7) that engages directly about the spinal rod 26 and a C-shaped coupler clamp 36 that overfits and locks yoke 35 to spinal rod 26. The coupler clamp and yoke combination permits positioning of coupler clamp 36 on spinal rod 26 at angles different than perpendicular to within plus or minus 18°. This allows for flexibility during surgical operations.

The pressing or compression means of instrument 10 for attaching coupler clamp 36 to rod 26 includes a plunger 38 preferably comprising a cylindrical rod slidably disposed within an axial passageway 40 in body handle 12. Plunger 38 is partially exposed via slot 39 in body handle 12 (see FIG. 3). During use, plunger 38 is slid axially against coupler 36 to compress the coupler into locking attachment with rod 26.

A cam handle 48 is pivotally connected to main handle 12 so that cam handle 48 pivots in the same directions as handle 12 and lever handle 14. Cam handle 48 pivots about a pivot such as pin 50, which is located at a position offset from pivot pin 16.

As shown in FIG. 3, cam handle 48 includes a projection such as cam blade 52 that interfits into slot 39 and into an open slot 54 in plunger 38. Cam blade 52 is oriented so as to slide plunger 38 toward distal end 18 of body handle 12 when cam handle 48 pivots toward handle 12.

Figure 7:
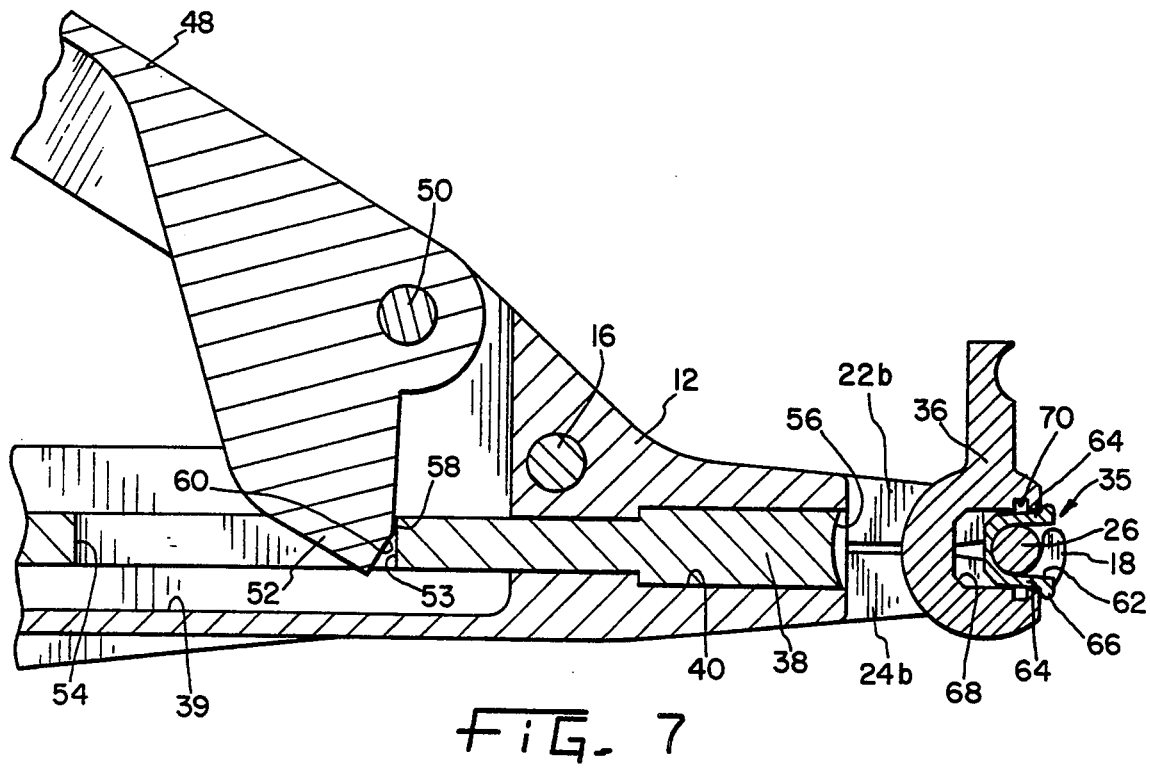
FIG. 7 is an enlarged fragmentary sectional view of the instrument prior to compression of the spinal coupler.

When squeezed, instrument 10 operates in a two stage manner. The first stage closes the jaws 22 and 24 together when the lever handle 14 is pulled upwardly toward handle 12. The second stage occurs as cam handle 48 is pivoted downwardly toward handle 12 thereby pushing plunger 38 and sliding it toward distal end 18 into pressing engagement with a spinal coupler 37 (FIG. 7).

Axial passageway 40 at proximal end 20 of body handle 12 includes an enlarged counterbored recess 42 about plunger 38 (FIG. 3). Within recess 42 is located a biasing means such as a spring 44. Spring 44 is disposed around plunger 38 and retained in recess 42 by a control knob 46 threadedly attached on the proximal end of plunger 38. The bias of spring 44 and the orientation of pivot pins 16 and 50 are such to permit one hand operation of instrument 10. Further, spring 44 is utilized to urge apart handle 12 and handle 14 when instrument 10 is not gripped about rod 26.

Control knob 46 may be rotated on plunger 38 to change the bias force of spring 44 experienced by plunger 38. Control knob 46 acts as a stop to prevent over extension of plunger 38 during instrument actuation, by interfering with proximal end 20 of handle 12. Further, control knob 46 operates as a visual indicator to the user that the compression operation is complete when it engages distal end 20 of handle 12. The bias force on plunger 38 creates a certain level of gripping tension on handle 48.

In operation, the present invention will couple a spinal coupler 36 to a rod 26 as shown in FIGS. 5–8. Spinal rod 26 will first be inserted into a patient, adjacent the spine. The surgeon will then fit a Modulock TM yoke 35 and coupler 36 over rod 26 into a particular position necessitated by the condition of the patient.

The surgeon will then grasp instrument 10 and adjust control knob 46 to the proper location by rotating control knob 46 about plunger 38 to adjust the amount of travel of plunger 38. Rotation of control knob 46 will either compress or expand spring 44. The surgeon will place instrument 10 into engagement with rod 26 so that rod 26 closely aligns into grooved portions 28 of jaws 22 and 24. Ramp sections 30 and 32 will assist the surgeon in guiding the rod 26 and instrument 10 into the proper position. Instrument 10 engages and attaches to rod 26 on both sides of coupler 36 thereby preventing axial movement of coupler 36 on rod 26. Jaw legs 22a, 22b, 24a, and 24b surround coupler 36 and firmly engage rod 26.

As the surgeon squeezes instrument 10 like a pair of pliers, jaws 22 and 24 close together thereby positively locating the instrument 10 and coupler 36 on rod 26. FIGS. 5 and 7 show this intermediate stage. Forked jaws 22a, 22b and jaws 24a, 24b grasp rod 26 tightly when instrument 10 is squeezed.

As handle 48 is further squeezed by the surgeon, it pivots about pivot pin 50. Blade 52 on cam handle 48 rotates about pivot pin 50 and engages surface 53 of opening 54 in plunger 38, thereby axially moving plunger 38 toward coupler 36 and rod 26 until knob 46 stops against end 20 of handle 12.

Figure 8:
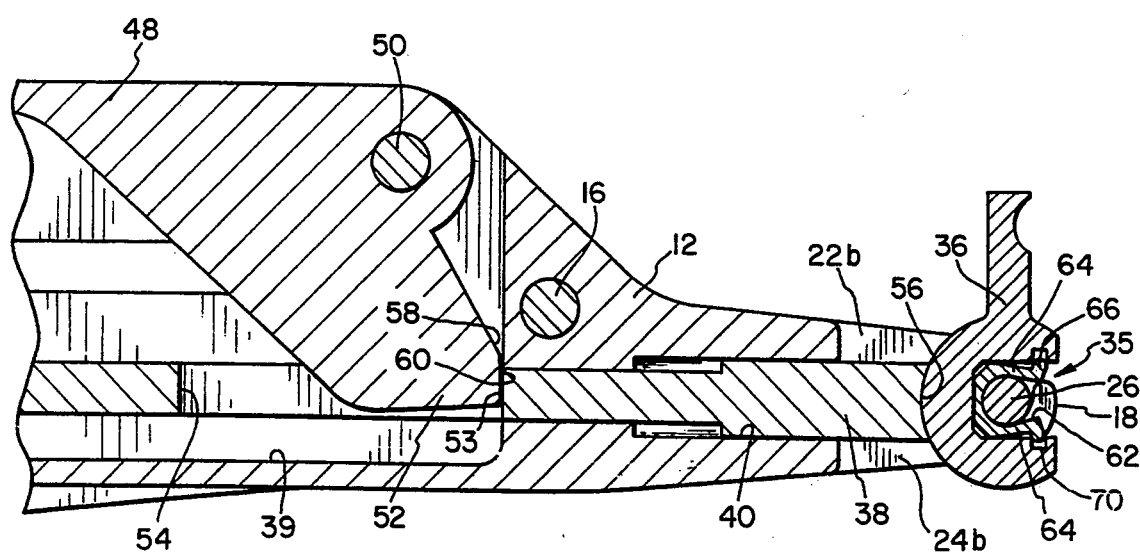
FIG. 8 is a fragmentary sectional view of the instrument after compression of the spinal coupler.

FIGS. 7 and 8 show cam blade 52 having two engagement surfaces 58 and 60. Engagement surface 58 contacts with surface 53 of plunger 38 during the initial stage of the compression operation. As cam handle 48 is pivoted from its starting position, engagement surface 58 causes plunger 38 to slide toward coupler 36. At a point during pivoting, engagement surface 60 engages plunger surface 53 changing the point of contact between cam blade 52 and plunger 38 thereby further increasing the force applied to coupler 36.

Instrument 10, as shown in FIGS. 6 and 8, is fully actuated or closed such that plunger 38 is fully extended out of handle 12. This extension of plunger 38 transmits a compression force from the front face 56 of plunger 38 onto coupler clamp 36 thereby connecting yoke member 35 and coupler clamp 36 to spinal rod 26 via an interference fit.

As shown in FIG. 7, yoke 35, having internal opening 62, is interfit or snapped over rod 26. Yoke 35 includes a pair of legs 64 having a flange 66 extending outwardly and generally perpendicular from legs 64. C-shaped clamp member 36 includes a recess 68 having a slot 70 into which flange 66 of yoke member 35 may interfit and lock. Prior to compression, clamp member engages yoke member 35 within recess 68 holding it in place on rod 26 (FIG. 7).

When clamp member 36 is compressed toward rod 26, yoke member 35 slides further into recess 68 until yoke flange 66 seats within slot 70. This orientation compresses leg 64 about rod 26 creating an interference fit thereby securing both yoke member 35 and clamp member 36 to rod 26.

The compression coupling force utilized by the instrument originates from the hand of the surgeon and is transmitted to cam handle 48, then to plunger 38. This coupling force is quite strong because of the leverage created by handle 48 and the action of cam surfaces 58 and 60. Sufficient force is generated and transmitted to prevent coupler 36 from separating yoke 35 from rod 26 after assembly. Plunger 38 effectively delivers a high compression force to the coupler 36 without loss of control or accuracy. Instrument 10 assures that the compression force is precisely applied without coupler 36 or instrument 10 sliding along rod 26.

While this invention has been described as having a preferred design, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. A surgical device for engaging a spinal rod and for coupling a spinal rod coupler to said rod, said device comprising:
    attaching means for temporarily securing said surgical device on the spinal rod and locating the spinal rod coupler against the spinal rod; and
    compression means for coupling the spinal rod coupler to the spinal rod by compressing the spinal rod coupler onto the spinal rod whereby an interference fit is formed therebetween, the compression means being pivotally connected to the attaching means by a pivot pin and operating independently from the attaching means.

2. The device of claim 1 in which said attaching means includes at least two jaws adapted to grip the spinal rod therebetween and serve to locate the spinal rod coupler against the spinal rod.

3. The device of claim 2 including a pair of handles and in which each said jaw is attached to a handle, said jaws held in opposed relationship to one another by said handles, said handles connected together in a scissors-like fashion.

4. The device of claim 1 in which said compression means includes a plunger adapted to engage the rod coupler and compress together the rod coupler and the spinal rod.

5. The device of claim 4 in which said plunger includes a rotatable control knob stop to prevent overextension of said plunger.

6. The device of claim 4 in which said compression means includes a handle that engages said plunger, said handle adapted to press said plunger into contact with the rod coupler to connect the rod coupler to the spinal rod by an interference fit.

7. A surgical device for engaging a spinal rod and for coupling a spinal rod coupler having a clamp member and an interfitting yoke member to the spinal rod, said surgical device comprising:
    a base handle having a first jaw;
    a lever handle having a second jaw, said lever handle connected in scissorlike fashion to said base handle so that said first and second jaws oppose one another and are configured to attach to opposite sides of the spinal rod; and
    means for pressing the clamp member of the spinal rod coupler onto the spinal rod thereby forming an interference fit between said yoke member and the spinal rod, said means for pressing includes a plunger for engaging said clamp member of the spinal rod coupler for connecting the spinal rod coupler and the spinal rod together, said plunger slides within said base handle and is operatively connected to a cam handle, said cam handle hinged to said base handle, such that when said cam handle and said base handle are closed together, said cam handle forces said plunger into contact with the clamp member of the spinal rod coupler, the cam handle and plunger being operable independently from the lever handle.

8. The device of claim 7 in which said first and second jaws are each adapted to grip the spinal rod in at least two places and locate the rod coupler between themselves and the spinal rod.

* * * * *